(12) United States Patent
Kuusela et al.

(10) Patent No.: US 6,396,416 B1
(45) Date of Patent: May 28, 2002

(54) ADD-ON UNIT FOR CONNECTING TO A MOBILE STATION AND A MOBILE STATION

(75) Inventors: Tom Kuusela; Timo Kaila, both of Turku (FI)

(73) Assignee: Nokia Mobile Phones Ltd., Espoo (FI)

( * ) Notice: Subject to any disclaimer, the term of this patent is extended or adjusted under 35 U.S.C. 154(b) by 0 days.

(21) Appl. No.: 09/202,169

(22) PCT Filed: Jun. 16, 1997

(86) PCT No.: PCT/FI97/00378

§ 371 (c)(1),
(2), (4) Date: Apr. 2, 1999

(87) PCT Pub. No.: WO97/49077

PCT Pub. Date: Dec. 24, 1997

(30) Foreign Application Priority Data

Jun. 17, 1996 (FI) .............................................. 960362 U

(51) Int. Cl.[7] .......................... G08C 17/00; G08C 19/12
(52) U.S. Cl. ............................... 340/870.28; 340/573.1; 128/903; 128/904; 600/301
(58) Field of Search ....................... 340/870.28, 573.1, 340/870.16, 870.07; 128/903; 607/32; 600/301

(56) References Cited

U.S. PATENT DOCUMENTS

| | | | | |
|---|---|---|---|---|
| 5,050,612 A | * | 9/1991 | Matsumura | 600/483 |
| 5,417,222 A | * | 5/1995 | Dempsey et al. | 128/696 |
| 5,772,586 A | | 6/1998 | Heinonen et al. | 600/300 |
| 5,787,341 A | | 7/1998 | Parkas et al. | 455/90 |
| 5,797,102 A | | 8/1998 | Hallikainen et al. | 455/557 |
| 5,799,255 A | | 8/1998 | Berg et al. | 455/551 |

FOREIGN PATENT DOCUMENTS

| | | |
|---|---|---|
| FR | 2710438 | 3/1995 |
| JP | 307803 | 11/1995 |
| WO | WO 93/12604 | 6/1993 |
| WO | WO 94/01039 | 1/1994 |

* cited by examiner

*Primary Examiner*—Timothy Edwards
(74) *Attorney, Agent, or Firm*—Perman & Green, LLP

(57) ABSTRACT

An auxiliary unit, adapted to be coupled to a mobile station comprising a basic element containing components necessary for data transmission, analyses and storage, as well as a sensor element containing a sensor suitable for the non-invasive measuring of a person's bodily functions and the special electronics required by the sensor. This means that different kinds of non-invasive measurements, such as ECG, EEG, EMG, blood pressure and respiratory flow, can be taken by changing the mere sensor element.

24 Claims, 6 Drawing Sheets

ADD-ON UNIT FOR CONNECTING TO A MOBILE STATION AND A MOBILE STATION

The present invention relates to an auxiliary unit, to be coupled to a mobile station, and the mobile station.

Information on patients' bodily functions has already previously been sent by phone from a measuring point to a nursing unit. International Patent Publication WO 94/01039 describes the transmission of a patient's ECG at a digital radio frequency from a measuring point (patient) to a nursing centre. The publication describes a new type of sensor for recording the ECG.

Digital mobile stations, such as portable GSM mobile phones, provide entirely new opportunities to control remotely patients' different kinds of bodily functions. The technical problem has been that the follow-up of different kinds of bodily functions requires several different types of auxiliary devices to be coupled to a transmitter, which mostly carry the same electronics but have different kinds of sensors, of course.

An auxiliary device, to be coupled to a mobile station, has now been invented, the device having a separate sensor element, which is replaced according to the bodily function measured at a given moment.

Thus, the object of the invention is an auxiliary unit intended to be coupled to a digital wireless telephone. This auxiliary unit comprises a basic element, which contains the components necessary for data transmission, analyses and storage. The auxiliary unit also comprises a sensor element, which contains a sensor suitable for the non-invasive follow-up of a person's bodily functions, as well as the special electronics required by this sensor.

The auxiliary unit, according to the invention, is characterised in that it comprises a basic element, which contains components necessary for data transmission, analyses and storage, and a sensor element, which contains a sensor suitable for non-invasive measurement of a person's bodily functions, as well as special electronics required by the sensor. The mobile station, according to the invention, is characterised in that it comprises components necessary for data transmission of a non-invasive measurement, analyses and storage, a sensor element, to be coupled thereto detachably, which contains a sensor suitable for non-invasive measurement of a person's bodily functions, as well as special electronics required by this sensor.

Figure 1:
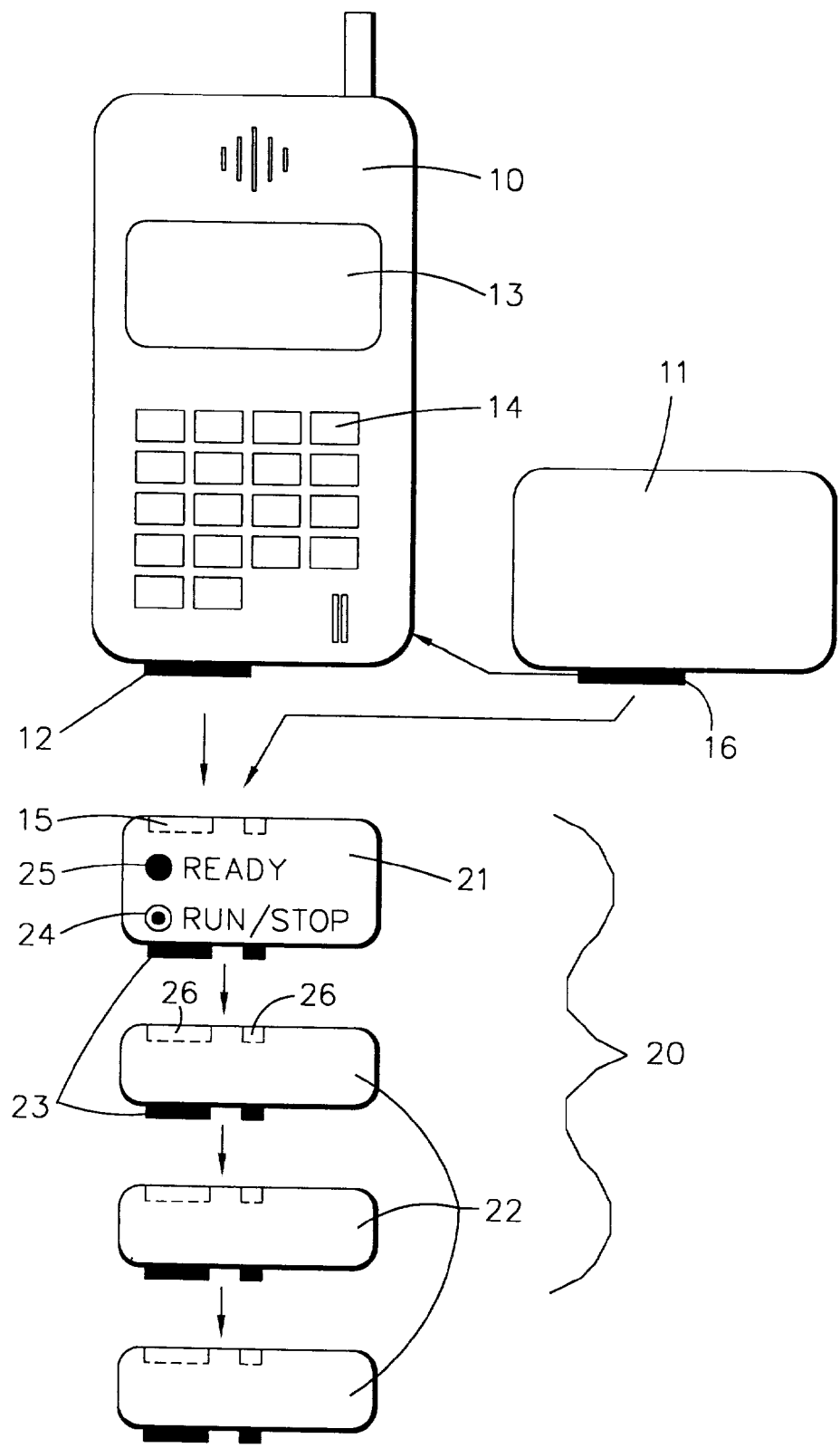
Figure 2:
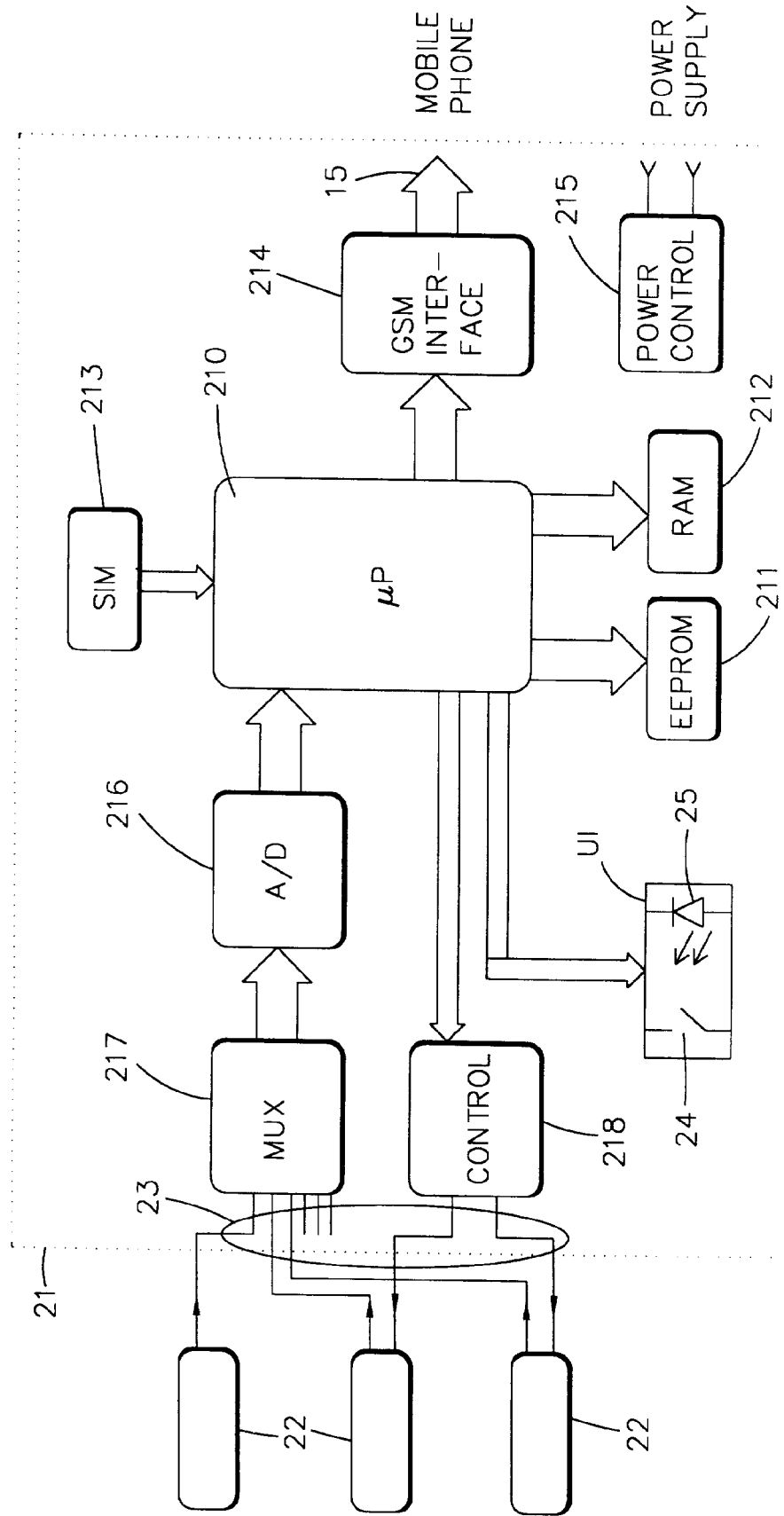
Figure 3:
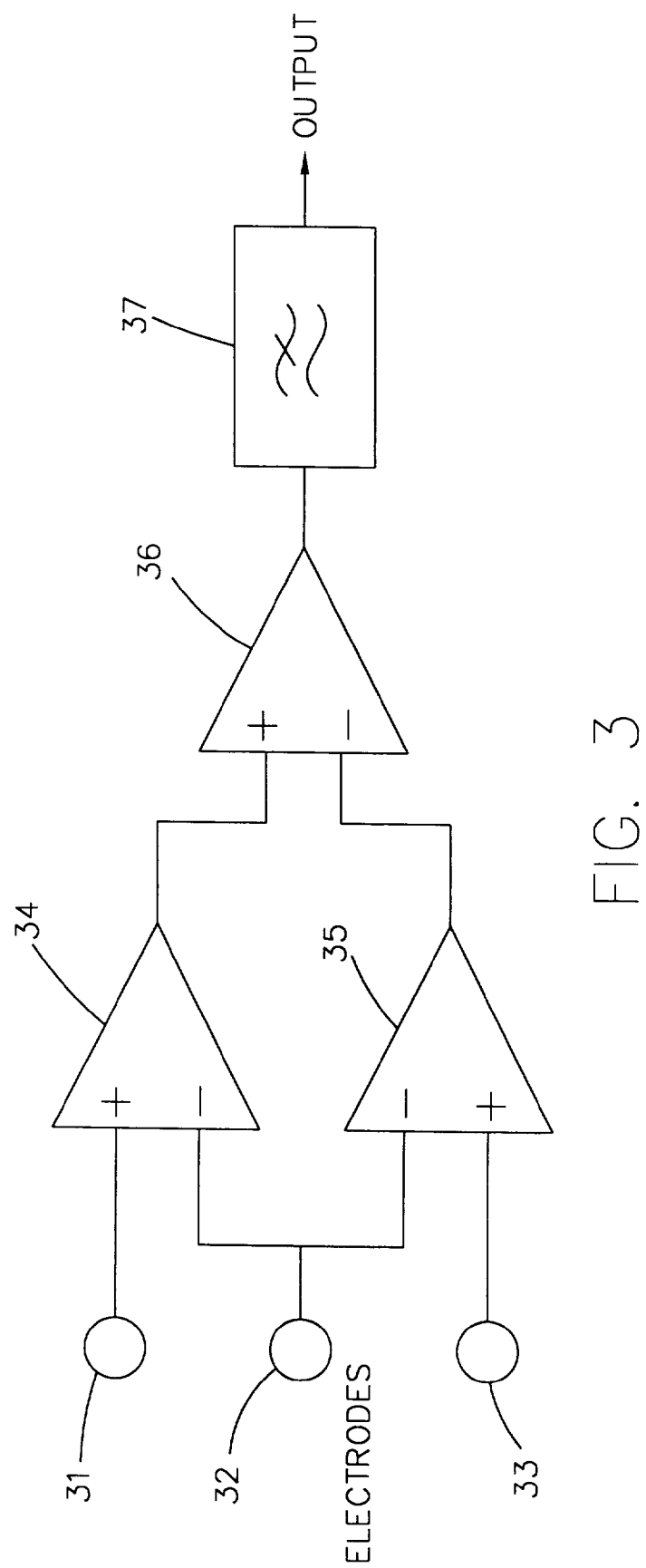
Figure 4:
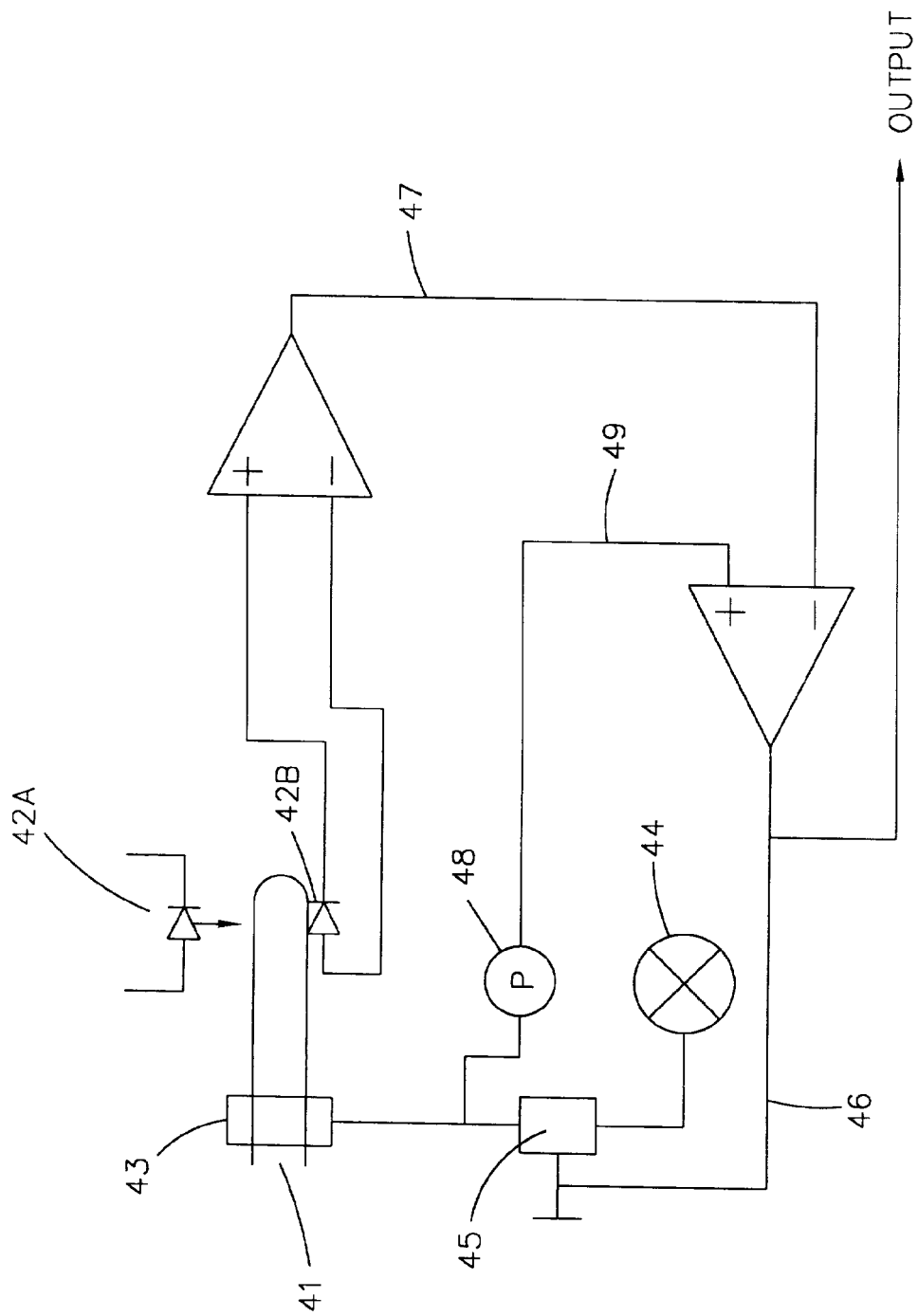
Figure 5:
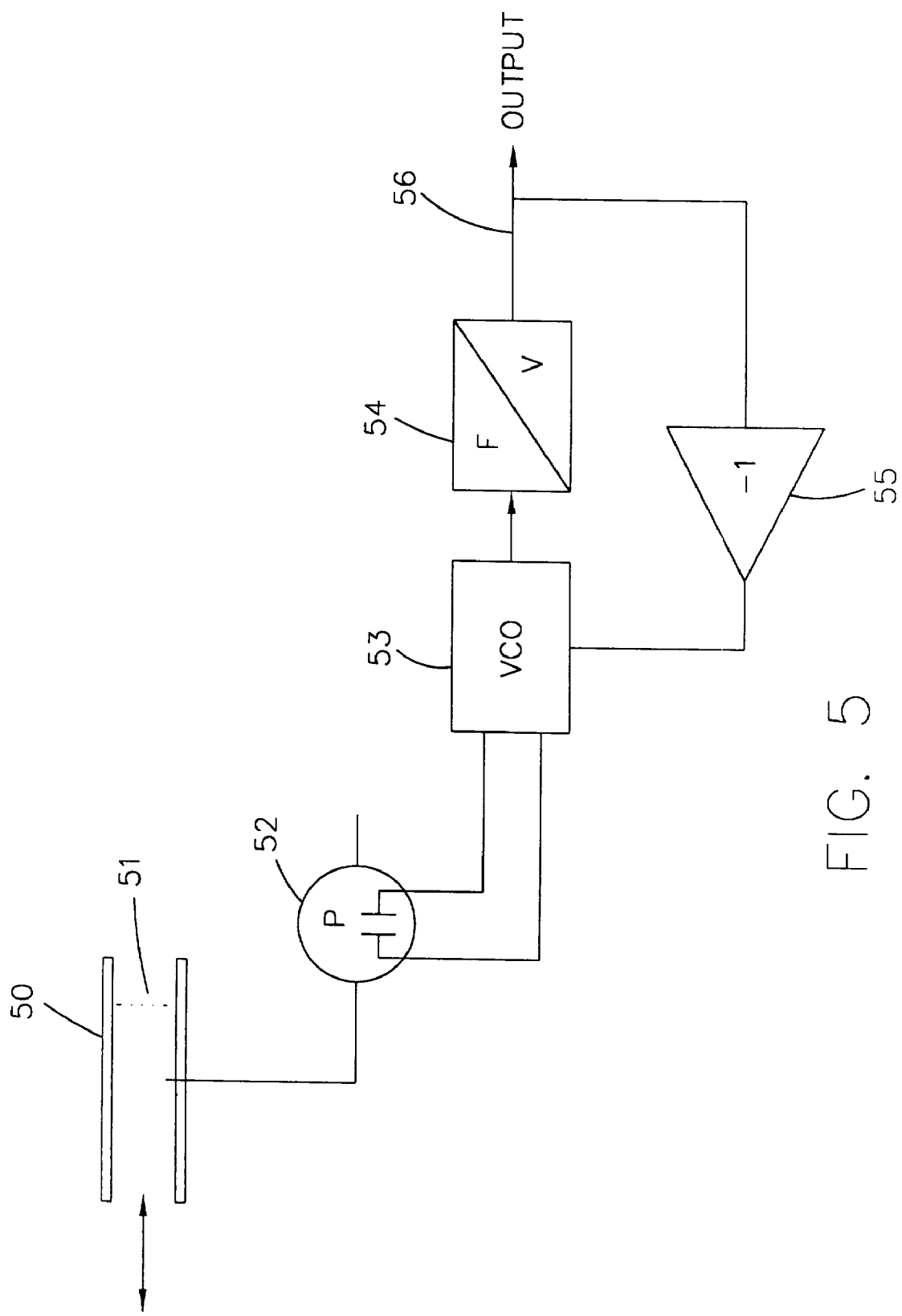

The invention will be discussed below in detail by referring to the enclosed drawings, of which FIG. 1 illustrates the assembly of equipment according to the invention, FIG. 2 illustrates the implementation of a basic unit as a block diagram, FIG. 3 illustrates a sensor unit intended for the recording of the ECG, EEG and EMG, FIG. 4 illustrates a sensor unit intended for the measuring of a blood pressure, and FIG. 5 illustrates a sensor unit intended for the measuring of respiration.

Figure 6:
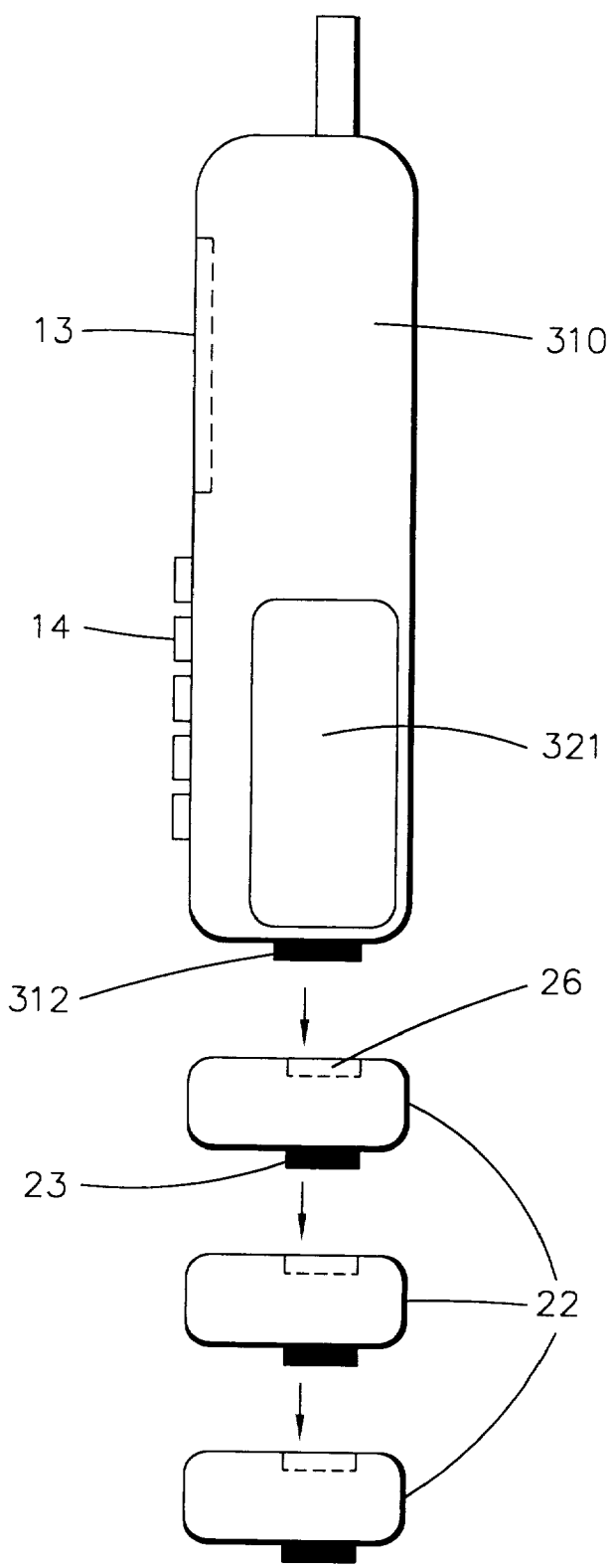

FIG. 6 illustrates the basic unit integrated as part of a mobile station and the sensor units coupled directly to the mobile station.

FIG. 1 illustrates the different elements of the inventions; a mobile station, such as a mobile station 10, whereto an auxiliary unit 20 according to the invention can be coupled, which in turn comprises at least two elements, i.e., a basic element (basic unit) 21 and a sensor element (sensor unit) 22, which can be easily replaced according to the function measured or several of them can be connected in sequence.

The basic unit 21 and the sensor unit 22 are coupled to the mobile station 10, e.g., to a digital GSM mobile phone utilising a data connection 12 included therein. If necessary, several sensor units 22 can be connected to the basic unit 21 in a pile, as illustrated in FIG. 1, by equipping the sensor units 22 with the same kind of connection as the basic unit 21.

The function of the basic unit 21 is to launch the measuring of the required bodily functions, to carry out the digitising of the measuring signals, to store the measuring results in a memory and, if necessary, to transmit these results, by mobile phone, to a nursing unit in the required form. If necessary, the basic unit 21 directs the user with the help of a display 13 of the phone and receives the user's commands through a keyboard 14 of the phone. The basic unit also produces the operating voltages required by the sensor units either from the power supply (battery) of the mobile phone or from a separate power supply unit 11, which can be coupled to the basic unit.

The sensor units 22 contain the measuring units, the couplings included, relating to each bodily function, as well as the necessary measuring and control electronics so that the unit could produce, for the basic unit 21, an initial analogue voltage proportional to the measuring quantity. The sensor units 22 also contain an internal analogue and digital combination bus 23 by means of which the control and measuring signals of the units, located farther down in the sensor unit pile, are transmitted to the basic unit. The operating voltages, required by the sensor units, which are produced, e.g., in the basic unit, are also transmitted through this bus 23. The sensor units 22 have been implemented so that the basic unit 21 is automatically capable of recognising which sensor units have been coupled thereto. Recognition can be carried out on the basis of a signal received from the sensor unit or, e.g., so that a bus connector 23 comprises several connectors, whereupon a different sensor unit produces a signal for a different connector. An output connector 23 of the bus is connected to an input connector 26. The connection of the bus 23 to the mobile phone is established through a basic unit 15 and the phone's data connection 12.

If necessary, the sensor unit pile and the basic unit can also be used without the mobile phone 10 which, in this case, can be replaced by a power supply unit 11 to be connected to the basic unit. This unit can be a battery packet made using a similar technique than in the mobile phone. Thus, in this case, the power supply unit 11 can also be a battery, coupled to the mobile phone, to be connected to the battery space of the mobile phone through a connector 16. The basic unit, according to the present invention, can also be integrated as part of the battery 11, to be coupled to the mobile phone, so that the basic unit's electronics and battery cells are within the same case. Thus, this kind of integrated auxiliary unit can be used independently or coupled to the mobile phone, whereupon the battery 11 feeds energy to both the mobile phone 10 and the basic unit 21, as well as to the sensor units 22 coupled thereto. In this case, data are preferably transmitted between the mobile phone and the basic unit through the connectors located within the mobile phone's battery space.

The advantage of the structure is that the use of different kinds of sensors does not require several different kinds of versions of the complicated basic element. The basic element 21 contains appropriately analog/digital converters, a microprocessor for controlling the operations, as well as a memory for storing the data. The memory is preferably non-volatile. The microprocessor is responsible for the measuring protocols, the analysing of the results and the data traffic to the telephone. The basic element can also contain a subscriber identity module (SIM), wherein the user's patient information, the nursing unit's identifiers, etc. have been stored.

In addition to the sensor itself, the sensor element 22 also contains the cables belonging thereto and, appropriately, also the differential amplifiers and filters for the signal of the measured bodily function.

Below we will discuss, by way of example, the implementation of the basic unit and different kinds of sensor units by referring to FIGS. 2–5.

FIG. 2 illustrates, in the form of a block diagram, the implementation of the basic unit presented above. The unit has, as a central component, a microprocessor 210 which controls the operation of an auxiliary unit, according to the invention, and the function of which is to provide for the measuring protocols, the analysing of the results and the data traffic to the mobile phone. The non-volatile memory is preferably an EEPROM circuit 211, which contains the microprocessor's program for carrying out the different operations, as well as possible calibration tables for the sensors. The memory 211 is also used for longer-term storage of the measuring results. Typically, the capacity of the EEPROM circuit is several dozen kilobytes. In addition, a RAM circuit 212 is used as a memory, the RAM circuit being used for operations required by the program, as well as for temporarily storing the measuring results and the result of the analyses normally while the microprocessor is performing a program retrieved from the memory 211.

A subscriber identity module (SIM) 214, used in GSM telephones, is preferably coupled to the mobile phone 10. In FIG. 2, it has been presented as part of the basic unit in order to illustrate its utilisation for an auxiliary unit, according to the invention, whereupon the SIM 214 can contain the patient's identity information, the identifiers of the nursing unit, the limit and emergency values relating to different bodily functions, etc. In this case, these data are transmitted to the basic unit through the mobile phone's data connection 12. Alternatively, the basic unit contains a separate, replaceable intelligent card 214 of its own, which is, e.g., of the size of a small subscriber identity module and wherein the above-mentioned data are stored.

For connecting the basic unit to the mobile phone, the basic unit has a mobile phone connection block 214, which provides for the electric adaptation of the signals and the data between the phone and the basic unit. Hence, the connection block 214 can be implemented in the same way as the data cards known in connection with the mobile phone, which carry out the adaptation of the data. An operating voltage generating element 215, illustrated in FIG. 2, produces from the output voltage, provided by the mobile phone or the separate power supply unit 11, the operating voltages required by the sensor units, e.g., according to the switchmade power supply principle. This unit also provides for the sensor elements' power consumption automation. An analog-digital converter block 216 converts the analogue voltages, coming from the sensor units, into a digital form. The converter 216 is, e.g., a 12-bit converter and its conversion speed is 200–500 samples a second. The connection between the bus 23 and the basic units' other components is implemented by means of an analogue multiplexer 217 which selects, controlled by the microprocessor, the signal of the sensor unit which should be digitised at a given moment. The connection between and the combination of the multiplexer 217 and the AD converter 216 is so fast that it is possible to serve several sensor units 22 simultaneously.

In addition to the microprocessor 210, the basic unit may contain a separate control unit 218, which provides for the control signals of the sensor units that need to be controlled by the processor during measuring. Alternatively, this operation can be carried out directly under the control of the microprocessor.

The basic unit has a push button 24 as a simple user interface Ul. By pressing the button, the user of the device can inform of the commencement or termination of measuring. In addition, the unit has a multicoloured signal light 25, which informs the user whether the equipment is in working order, whether the sensors have been correctly connected and whether the signal coming from the sensor unit is appropriate. In addition, by means of the signal light 25, it is also possible to inform of the measuring session's time of termination. The push button and the signal light together enable the device to be used without a mobile phone. If a mobile phone has been coupled to the equipment, it is possible to carry out the corresponding operations by means of a keyboard 13 and a display 14.

In the following, we will discuss, by way of example, three different implementations of a sensor unit suitable for the non-invasive measuring of a biosignal.

FIG. 3 illustrates a sensor unit suitable for recording an electrocardiogram (ECG), an electroencephalogram (EEG) and an electromyogram (EMG). The recording of these three electrograms is similar, in principle, because all of them measure small potential differences between electrodes placed on the skin (typically, in the case of an ECG, hundreds of microvolts, whereas in the case of an EEG or EMG, microvolts or dozens of microvolts). There are differences in the structure of the skin sensors, in the amplification required by the signals, as well as in the frequency filtering. FIG. 3 illustrates one possible typical connection, when using three sensors 31–33 to produce a single output voltage. The aim is to produce from the measuring signals, by means of differential amplifiers 34–36, as reliable a common reference potential as possible, against which one or more measuring signals are measured. The bus structure between the sensor units and the basic unit also allows multichannel measuring if necessary. A low-pass filter 37, included in the unit, removes, from the measuring signals, the high (interference) components hindering the analog-digital conversion, after which the signal is lead from the sensor unit output to the basic unit.

As for the ECG, the software of the basic unit includes the detection of a characteristic tension pulse (so-called ORS complex) produced by the heart beat and, through it, the computation of the average pulse density, which is carried out by means of the microprocessor 210. In addition, some clear functional disturbances of the cardiac muscle can be deduced from the shape of the pulse in question, of which the device can inform the user. A momentary heart rate and the original ECG signal (sampling speed 200 samples a second, resolution 12 bits) are stored in the memory 211. A typical measuring period lasts for a few minutes. In long-term registration (e.g., 24 hours), only a momentary heart rate is stored.

FIG. 4 illustrates a sensor unit suitable for measuring a blood pressure. In this sensor structure, a continuous blood pressure is measured from a person's finger 41. The equipment consists of an infrared transmitter-receiver pair 42a, 42b, by means of which the blood amount in the finger is measured and, through it, the blood pressure in the finger, as well as of a pneumatically operated finger sleeve 43. The aim is to continuously produce in the sleeve 43, by means of an air pump 44, a pressure which precisely compensates for the variation of pressure caused by the circulation. In this situation, the intensity of the IR radiation penetrating the finger remains stable. In this case, a control voltage 46 of an adjusting valve 45, included in the system, is directly proportional to the blood pressure. To ensure that the scope of dynamics of the adjustment would be as wide as possible, in addition to a signal 47 of the IR detector 42b, the magnitude of the adjustment of the valve 45 is also established on the basis of a pressure signal 49 of the sleeve. For this purpose, the equipment also includes a pressure sensor 48 which measures the pressure of the sleeve.

The function of the basic unit's software, relating to blood pressure, is to adjust before the actual measuring begins the basic pressure of the sleeve so that the required scope of dynamics is reached. After this, the software should detect the minimum and maximum value (i.e., so-called diastolic and systolic blood pressure) of the blood pressure pulse relating to each heart beat and compute the actual pressure values on the basis of the calibration values. The activities of the softwares (stored in the EEPROM memory 211) are carried out by means of the microprocessor 210. The pressure values are transmitted from the sensor output to the basic unit as a voltage. If the equipment also contains an ECG unit, it is possible to combine the two acts of measuring, whereupon detection becomes easier.

FIG. 5 illustrates a sensor unit suitable for measuring respiration. The function of the unit is to measure the flow of a person's inhalation and exhalation. This is done by blowing into a straight pipe 50 that has a coarse-meshed net 51 installed at its other end. While the air flows through the net either over-pressure (exhalation) or under-pressure (inhalation) is produced in relation to the outside air pressure. This pressure differential is proportional to the flow. The pressure differential is measured using a capacitive pressure differential sensor 52. The capacitance in question is part of a voltage controlled oscillator (VCO) 53. When the pressure changes, the capacitance in question also changes, whereupon the frequency of the oscillator changes. The output signal of the oscillator has been connected to a frequency-voltage converter 54 from the output of which a voltage signal, directly proportional to the frequency, is obtained. This control voltage has been connected through a possible frequency changing multiplier 55 to a control input determining the frequency of the VCO. The final result is that the control voltage automatically settles at such a value that the frequency of the oscillator remains stable although the capacitance of the pressure differential sensor changes. A control voltage 56, produced by the converter, which is lead to the basic unit as the sensor unit's input is, thus, proportional to the pressure differential and, through it, to the respiratory flow.

Because the measuring of the flow presented above is rather non-linear, the software of the basic unit must correct the measuring result to genuine flow readings using, e.g., a calibration table. After this, the flow signal is integrated over time, whereupon the momentary air volume of the lungs is obtained. Both the flow and volume signal can be stored for further analyses. In addition, the maximum inhalation and exhalation flow can be computed on the basis of the flow signal (so-called PEF and PIF measuring). These corrections, integrations and computations are carried out by means of the microprocessor 210.

Other possible quantities describing bodily functions can be, e.g., body temperature (with a thermoelement, etc.), oxygen content of the blood (the absorption of oxidised and inoxidised blood is measured from the auricle using two characteristic wavelengths of visible light and their quotient is computed), blood sugar level, heart and breath sounds (using a sensitive microphone).

The equipment 20 has two measuring modes which can be used for different kinds of measuring needs:

(a) A biosignal is measured for one minute or longer, and the entire measuring series, the possible results of the analyses included, is stored in the basic unit's non-volatile memory 211. These signals include, e.g., ECG, EEG, EMG, blood pressure and respiratory flow.

(b) The quantity is measured only for as long as it is necessary to obtain a reliable value. These include, e.g., momentary blood pressure, PEF/PIF, blood oxygen concentration, blood sugar concentration, temperature. In this case, it is a question of long-term follow-up (e.g., 24 hours). Only these individual values are stored in the memory 211 or 212.

The basic unit, according to the invention, can have, e.g., four different basic operating modes according to which the data, stored in the memory 211 or 212, can be processed in four different ways:

(1) After measuring, the user is presented, e.g., on the display 13 of the mobile phone, simple statistical results computed on the basis of the signal, such as the average pulse density and variability, the average systolic and diastolic blood pressure or the maximum inhalation/exhalation flow, as well as the possible notices of exceeded limit values or other abnormalities observed. After this, the material can be deleted from the memory. If necessary, the patient may contact the physician attending him by means of his mobile phone as normal.

(2) The data, collected by means of either the measuring mode (a) or (b), and the results of the analyses are sent by the user to a health centre or a central hospital, to the physician attending him, in the form of graphic telefax output which also contains the patient identifiers, etc. Thus, the physician can immediately visually study the behaviour of the vital function parameters and quickly give feedback to the user. The method does not require any special equipment other than telefax equipment at the receiving end.

(3) All the data are sent, through a mobile phone, to a nursing unit in the form of a digital file. This provides an opportunity to make more complicated and fundamental analyses of the measuring signals particularly in connection with multichannel measurements. The method requires that the receiving end has appropriate computer hardware, telecommunication connections included. This is also well suited for a (first aid) physician who uses the equipment as part of the initial treatment diagnostic devices.

(4) The data, collected by means of either the measuring mode (a) or (b), are transferred to a nursing unit without the user of the equipment sending them. This remote discharge method enables patients in poor health, in particular, to be watched over round-the-clock, if necessary, provided that the equipment is equipped with the possibility of starting a measuring session by telephone. Also in this alternative, it is important that the physician and the patient are able to communicate orally.

Individual measuring results can also be sent through a mobile phone in a short message which, in the GSM system, is known as a short message service (SMS). The invention can also be used for the non-invasive measuring of other bodily functions and for analysing and reporting the measuring results. This is done simply by replacing the sensor element. By miniaturising the sensor mechanics, the basic unit and the sensor unit can be made sufficiently small and light. As shown in FIG. 6, the basic unit 321 can also be integrated as part of a mobile station 310, whereupon the sensor units 22 are coupled directly to the mobile station 310 via data connector 312.

This paper presents the implementation and embodiments of the present invention with the help of examples. It is obvious to a person skilled in the art that the present invention is not restricted to details of the embodiments presented above, and that the invention can also be implemented in another form without deviating from the characteristics of the invention. The embodiments presented above should be considered illustrative, but not restricting. Thus, the possibilities of implementing and using the invention are only restricted by the enclosed claims. Consequently, the various options of implementing the invention as determined by the claims, including the equivalent implementations, also belong to the scope of the invention.

What is claimed is:

1. An auxiliary unit, for non-invasive measurement of a person's bodily functions, to be coupled to a mobile station, the auxiliary unit comprising a basic element and a sensor element, the basic element contains components necessary for data transmission, analyses and storage relating to non-invasive measurement of a person's bodily functions, wherein the sensor element contains a sensor suitable for non-invasive measurement for a person's bodily functions and measuring and control electronics required by this sensor, and wherein the sensor element is detachably coupled to the basic element, the basic element being further adapted to receive electrical signals from the sensor element related to the non-invasive measurements and convert the signals into a protocol suitable for use by the mobile station.

2. An auxiliary unit according to claim 1, characterised in that the basic element (21) and the sensor element (22) comprise means (23, 26) for connecting the sensor element to the basic element detachably.

3. An auxiliary unit according to claim 1, characterised in that the sensor element comprises means (23) for connecting another sensor element thereto.

4. An auxiliary unit according to claim 1, characterised in that the battery (11) has been arranged to feed energy to the auxiliary unit (20) and the mobile station (10) to be coupled thereto.

5. An auxiliary unit according to claim 1, wherein said special measuring and control electronics is configured to produce a signal proportional to the measuring quantity.

6. The mobile station of claim 1 wherein the basic element includes an analog to digital converter for converting the signals received from the sensor element.

7. The auxiliary unit of claim 1 wherein the special measuring and control electronics required by the sensor includes measurement and control electronics adapted to allow the sensor element to convert the measured bodily functions into signals suitable for use by the basic element.

8. The auxiliary unit of claim 1 wherein the special measuring and control electronics required by the sensor includes means for the sensor element to produce an initial analog voltage proportional to a measuring quantity corresponding to the bodily function being measured.

9. The auxiliary unit of claim 1 wherein the mobile station comprises a mobile telephone.

10. An auxiliary unit according to claim 1, characterised in that it has been integrated with a battery (11), to be coupled to a mobile station, comprising means (16) to be connected to a battery space of the mobile station.

11. An auxiliary unit according to claim 10, characterised in that the basic element (21) comprises means (210, 211, 214) for receiving and storing a signal proportional to measuring and for producing the measuring data.

12. An auxiliary unit according to claim 11, characterised in that the basic element (21) comprises means (210, 214) for processing the measuring data into a form to be transmitted through the mobile station (10).

13. A mobile station comprising means for transmitting data and comprising a sensor element for non-invasive measurement of a person's bodily functions detachably coupled to the mobile station, the mobile station comprises components necessary for non-invasive measuring data transmission, analyses and storage, the sensor element contains a sensor suitable for the non-invasive measuring of a person's bodily functions and measuring and control electronics required by this sensor, wherein the mobile station further comprises a means adapted to receive information from the sensor element and convert the information into a data format compatible with a receiving station.

14. The mobile station of claim 13 wherein the mobile station is adapted to transmit the converted information to a receiving station which is adapted to process the converted information.

15. The mobile station of claim 13 wherein the special measuring and control electronics includes means to allow the sensor element to convert the measured bodily functions into signals suitable for use by the basic element.

16. The mobile station of claim 13 wherein the mobile station comprises a mobile telephone.

17. An auxiliary unit adapted to be coupled to a mobile station comprising:
    a basic element including components necessary for data transmission, analyses and storage;
    a sensor element including a sensor suitable for non-invasive measurement of a person's bodily functions wherein the sensor element includes a connection device adapted to connect the sensor element to another sensor element; and electronics required by the sensor.

18. The auxiliary unit of claim 17 further comprising:
    an integrated battery adapted to be coupled to a mobile station; and
    a connection device adapted to connect the integrated battery to a battery space of the mobile station.

19. The auxiliary unit of claim 18 further comprising a battery device that is adapted to feed energy to the auxiliary unit and the mobile station.

20. The auxiliary unit of claim 18 wherein the basic element further comprises a device adapted to receive and store a signal proportional to a measurement signal and for producing measurement data.

21. An auxiliary unit, for non-invasive measurement of a person's bodily functions, adapted to be coupled to a mobile station, the auxiliary unit comprising:
    a sensor element including a sensor suitable for the non-invasive measurement of the person's bodily functions, the sensor including measurement and control electronics adapted to allow the sensor element to convert the measured bodily functions into signals suitable for use auxiliary unit; and
    a basic element including components for data transmission, analyses and storage of information related to the non-invasive measurement of the person's bodily functions, wherein the basic element is integrated with a battery device for the mobile station in a case, the battery device comprising means for being connected to a battery space of the mobile station, the basic element being further adapted to receive electrical signals from the sensor element related to the non-invasive measurements and convert the received signals into a protocol suitable for use by the mobile station; and wherein the sensor element is adapted to be detachably coupled to the battery device integrated with the basic element.

22. The auxiliary unit of claim 21 wherein the mobile station comprises a mobile telephone.

23. A mobile station comprising a battery and an auxiliary unit for non-invasive measurement of a person's bodily functions adapted to be coupled to the mobile station, the auxiliary unit comprising:

a basic element including components necessary for data transmission, analyses and storage of information related to the non-invasive measurement of a person's bodily functions;

a sensor element adapted to be detachably coupled to the mobile station, the sensor element including a sensor suitable for the non-invasive measurement of the person's bodily functions and control and measurement electronics adapted to allow the sensor element to provide the basic element with signals corresponding to the measured bodily functions; and a battery device of the mobile station wherein the basic element is integrated as part of the battery device in a battery device case, the battery device comprising means for connecting the battery device to a battery space of the mobile station, the basic element being further adapted to receive electrical signals corresponding to the measured bodily functions from the sensor element and convert the signals into a protocol suitable for use by the mobile station.

24. The mobile station of claim 23 wherein the mobile station comprises a mobile telephone.

* * * * *